United States Patent [19]
Frazee

[11] 4,016,308
[45] Apr. 5, 1977

[54] HUMIDITY SENSOR, MATERIAL THEREFOR AND METHOD

[75] Inventor: Lawrence E. Frazee, Norfolk, Nebr.

[73] Assignee: Plessey Incorporated, Melville, N.Y.

[22] Filed: Apr. 9, 1975

[21] Appl. No.: 566,350

[52] U.S. Cl. .................. 427/125; 252/514; 252/519; 338/35; 427/126; 427/287; 427/380; 427/383 B

[51] Int. Cl.² .......................... B05D 5/12

[58] Field of Search .......... 252/514, 519; 427/125, 427/126, 380, 383 B, 287; 29/620, 621; 338/35

[56] References Cited
UNITED STATES PATENTS

| | | | |
|---|---|---|---|
| 3,380,835 | 4/1968 | Short | 252/514 |
| 3,408,311 | 10/1968 | Short | 252/514 |
| 3,444,501 | 5/1969 | Delaney et al. | 252/519 |
| 3,553,109 | 1/1971 | Hoffman | 252/514 |
| 3,784,887 | 1/1974 | Sheard | 252/514 |
| 3,823,093 | 7/1974 | Amin | 252/514 |
| 3,838,071 | 9/1974 | Amin | 252/514 |

*Primary Examiner*—Cameron K. Weiffenbach
*Attorney, Agent, or Firm*—James J. Burke

[57] ABSTRACT

A novel humidity sensor printed and fired on a dielectric substrate comprising an interdigitated pattern of a conductive precious metal with cobalt oxide as the only binder. Sensors according to the invention may be employed as hermeticity detectors in semiconductor packages.

5 Claims, 4 Drawing Figures

HUMIDITY SENSOR, MATERIAL THEREFOR AND METHOD

BACKGROUND OF THE INVENTION

The present invention relates in general to humidity sensors or hygrometers and, more particularly, it relates to devices having electrical resistivity which is a function of relative humidity. Still more particularly, the invention relates to humidity sensors of the type described employing cobalt oxide.

U.S. Pat. No. 3,345,596 discloses a humidity sensor comprising a screened and fired layer of cobalt oxide on a dielectric substrate such as alumina, and with a screened and fired precious metal electrode, also including glass, on top of the cobalt oxide. To achieve hygroscopic properties the CoO must be fired at +1350° C. In practice, the electrode pattern is generally in the form of closely spaced, interdigitated fingers connected at their respective bases to form two electrodes.

In co-pending U.S. application Ser. No. 443,436, now U.S. Pat. No. 3,890,703 issued June 24, 1975, and assigned to the same assignee as the instant application, it is disclosed that humidity sensors of this type are improved if the cobalt oxide is subjected to a second firing in a reducing atmosphere. In co-pending U.S. application Ser. No. 426,953, also assigned to the same assignee as the instant application, further improvements including a porous Teflon (TM) coating over the sensor, and a fired-on heating element on the back of the sensor, are described.

OBJECTS OF THE INVENTION

A general object of the present invention is to provide a humidity sensor that is easier to construct than prior art devices.

Another object of the present invention is to provide a novel method of making humidity sensors.

A still further object of the present invention is to provide simple, reliable and inexpensive humidity sensors.

Still another object of the present invention is to provide a new thick film, material to make humidity sensors with.

A still further object of the present invention is to provide an improved hermeticity detector for semiconductor packages.

Various other objects and advantages of the invention will become clear from the following description of an embodiment thereof, and the novel features will be particularly pointed out in connection with the appended claims.

THE DRAWINGS

Reference will hereinafter be made to the accompanying drawings, in which.

DESCRIPTION OF EMBODIMENTS

The invention is based, in essential part, on the discovery that a good sensor can be constructed by adding cobalt oxide to the precious metal conductor paste, and screening and firing the mixture in the conventional, interdigitated conductor pattern. Thus, the separate screening and firing of cobalt oxide and electrodes is eliminated.

Sensors produced in accordance with the invention visually resemble conventional cobalt oxide hygrometers, in that the surface of the substrate between the electrodes has the familiar cobalt blue appearance. Microscopic examination shows that the cobalt oxide has diffused out from the printed area. Therefore, besides bonding the platinum to the substrate, the reaction of the cobalt oxide with the aluminum oxide substrate apparently forms a continuous hygroscopic layer between the platinum conductor fingers.

If the diffused film contains cobalt, as is believed either as the oxide or a complex cobalt-aluminate, then the mode of conduction between the electrodes would appear to be the same as is ascribed to conventional devices, i.e. on the surface. The fact that devices of the present invention are operable in both AC and DC circuits tends to favor this explanation.

Figure 1:
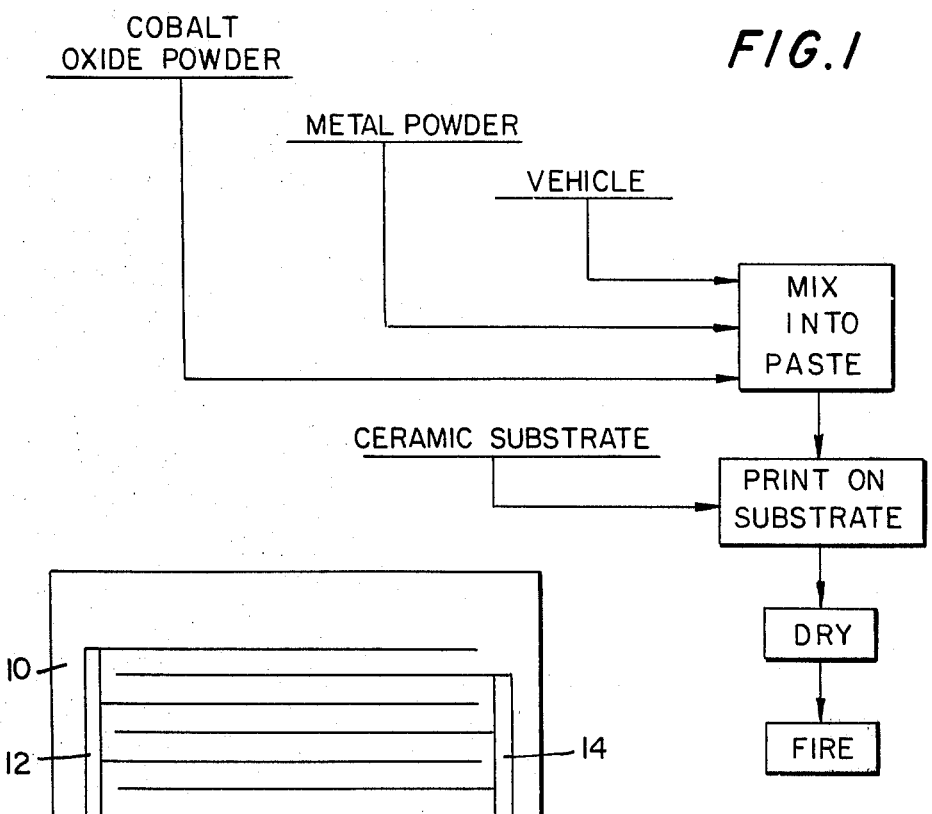
FIG. 1 is a flow sheet of steps carrying out the invention.

FIG. 1 illustrates the steps necessary to carry out the present invention. Commercially purchased cobalt oxide powder having a maximum particle size of −325 mesh is used. This powder includes minor proportions of cobalt oxides other than CoO, but only the latter will survive firing at +1000° C. For the metal constituent, precious metals are needed so that oxidation will not occur during firing or in use. Ordinary thick film conductor compositions such as platinum-gold, palladium-gold or platinum-palladium-gold alloys are satisfactory. A pure platinum powder is preferred, and a powder that melts below the firing temperature would not be chosen. The proportions of metal to oxide are not critical, other than that there should be at least 2% of CoO (dry basis, by weight) in the mixture, and 5–15% is preferred. As noted in Example hereinbelow, 20% CoO is satisfactory.

Figure 2:
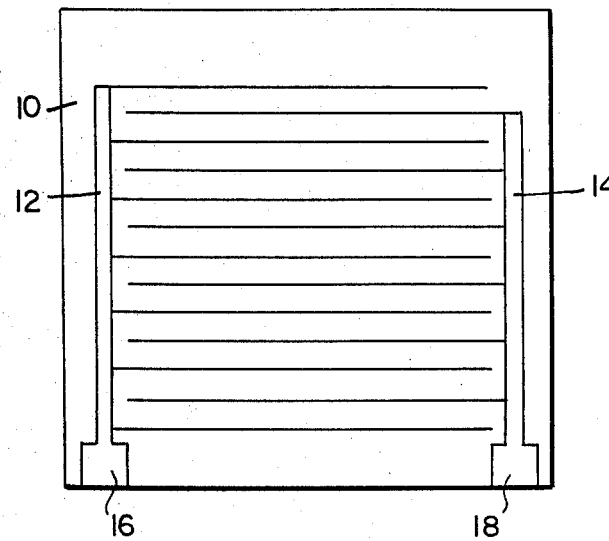
FIG. 2 is a plan view of an embodiment of the invention.

The organic vehicle is entirely conventional in the thick film art and needn't be described herein other than to note that such vehicles generally include a resinous binder dissolved in a volatile solvent, with or without added thickeners. The vehicle is added in sufficient quantity to produce a screenable paste, and the whole is milled together for an hour or more to eliminate any agglomerates. Screening onto the substrate follows. With reference to FIG. 2, the substrate 10 is usually 96% alumina. The interdigitated electrode pattern 12, 14 includes bonding pads 16, 18 for connection of the device in a circuit.

Air drying follows, during which time volatile constituents of the solvent will evaporate. This is followed by a conventional air-firing cycle, typically 1350°–1550° C. for about 5–15 minutes. The firing is below the melting point of any of the paste constituents, yet a very good bond to the substrate is achieved. While not wishing to be bound to any particular theory, it is considered possible that a complex, polynary oxide of the cobalt-aluminate type is formed at the interface, which could have a melting point the firing temperature. The literature identifies $CoAl_2O_4$ as a known compound of this type. Such a compound could play a role in the conduction mechanism of both conventional devices and devices in accordance with the invention, but this role, if it exists, is unknown.

After firing and cooling, hygrometers are ready for calibration and use.

Understanding of the invention will be facilitated by the following specific example, which is illustrative only and is not to be considered in a limiting sense.

EXAMPLE

A screen printable paste was formulated as follows:

|  |  | Wt. Pct. |
|---|---|---|
| Cobalt oxide powder (Fisher Scientific No. C382) |  | 16 |
| Pt powder (Matthey Bishop M, 1-2μ) |  | 69 |
| Vehicle |  | 15 |
| β-terpinol | 88.7% |  |
| Staybellite | 6.6% |  |
| Ethyl Cellulose | 4.7% |  |

The mixture was milled on a three roll mill for 0.5 hours. Patterns of the type illustrated in FIG. 2 and having an overall dimension of about 0.2 × 0.2 in. with 7.5 mils between adjacent electrodes were screened through a 325 mesh wire screen onto 96% $Al_2O_3$ substrates, dried in air for one hour and fired at 1500° C. for 7 minutes.

Figure 3:
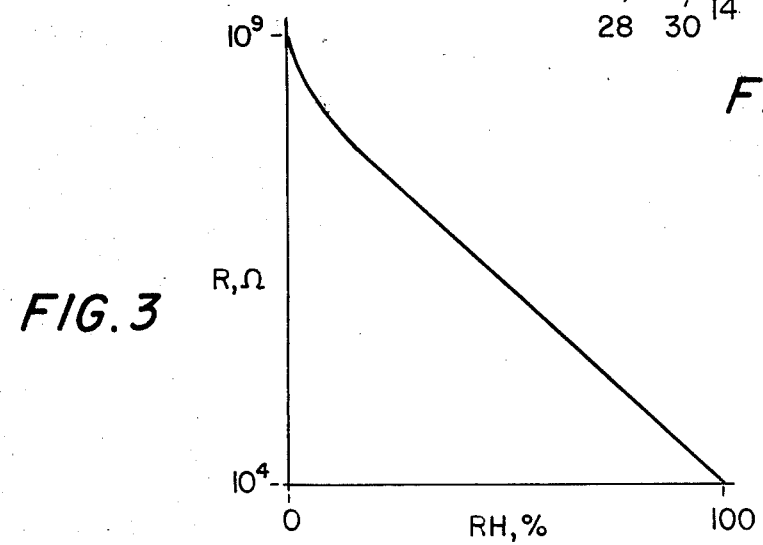
FIG. 3 is a plot of relative humidity vs. resistance of the sensor of the invention.

A response curve for one of these devices is shown in FIG. 3. As can be seen, while not quite linear it is a reasonably flat response. Further, the slope of the curve near 0% relative humidity makes the hygrometers of the present invention useful as hermeticity detectors in devices (optical, electronic, etc.) requiring such protection.

Figure 4:
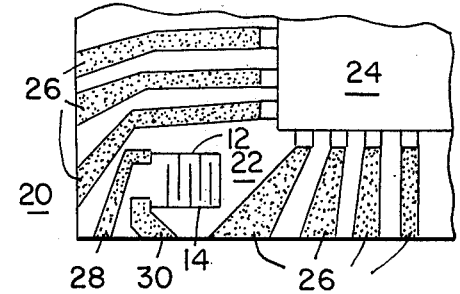
FIG. 4 is a partial plan view of a beam lead semi-conductor package employing the invention.

In the latter connection, the invention has particular utility as an on-line hermeticity detector in semiconductor packages, and attention is directed to FIG. 4, where a package 20, prior to being sealed, has visible within it a cavity 22 with a beam-lead integrated circuit chip 24 thereon, and corresponding metallized and plated lead patterns 26. Two leads 28, 30, however, terminate away from chip 24 and have printed and fired thereon an interdigitated electrode pattern 12, 14, just as shown in FIG. 2, of the composition of the present invention. Electrical connection to leads 28, 30 thus allows monitoring of package hermeticity on a continuous basis without testing and trouble-shooting the entire circuit. As an alternative, of course, the sensor may be connected into the circuit of chip 24, altering its operation upon seal failure.

As a further alternative, the embodiment of FIG. 2 may comprise a ceramic lid for a semiconductive device package.

Various changes in the details, steps, compositions and patterns, which have been herein described and illustrated in order to explain the nature of the invention, may be made by those skilled in the art within the principle and scope of the invention as defined in the appended claims.

What is claimed is:

1. The method of making a humidity sensor comprising:
   forming a screen-printable paste including, on a dry basis, at least 2 wt. % of finely divided cobalt oxide powder and a major proportion of a finely divided precious metal powder plus an organic vehicle;
   printing a pattern of said material onto a ceramic substrate in the form of interdigitated fingers;
   drying said pattern; and
   firing said pattern at a temperature in the range of 1350° to 1550° C. for about 5 to 15 minutes, said oxide diffusing out from printed pattern areas to form a continuous hygroscopic film between said fingers.

2. The method as claimed in claim 1, wherein said paste comprises on a dry basis 2 to 20 wt. pct. cobalt oxide powder and 80 to 98 wt. pct. precious metal powder.

3. The method as claimed in claim 1, wherein the particle size of said powders is no more than 200 mesh.

4. The method as claimed in claim 1, wherein said precious metal powder has a melting point above the firing temperature and is selected from the group consisting of gold alloys, platinum, palladium and mixtures and alloys of these metals.

5. The method as claimed in claim 1, wherein said pattern additionally comprises an integral bonding pad printed with each said electrode.

* * * * *

UNITED STATES PATENT OFFICE
CERTIFICATE OF CORRECTION

Patent No. 4,016,308　　　　　　　Dated April 5, 1977

Inventor(s) Lawrence E. Frazee

It is certified that error appears in the above-identified patent and that said Letters Patent are hereby corrected as shown below:

Column 2, line 65, after "point" insert -- below --.

Signed and Sealed this

Fourteenth Day of June 1977

[SEAL]

Attest:

RUTH C. MASON
*Attesting Officer*

C. MARSHALL DANN
*Commissioner of Patents and Trademarks*